United States Patent [19]

Fujitani et al.

[11] Patent Number: 4,801,620

[45] Date of Patent: Jan. 31, 1989

[54] CATALYST FOR HYDROCARBON SYNTHESIS

[75] Inventors: Yoshiyasu Fujitani; Hideaki Muraki; Shiroh Kondoh, all of Aichi, Japan

[73] Assignee: Kabushiki Kaisha Toyota Chuo Kenkyusho, Aichi, Japan

[21] Appl. No.: 912,216

[22] Filed: Sep. 26, 1986

Related U.S. Application Data

[62] Division of Ser. No. 791,064, Oct. 24, 1985, abandoned.

[30] Foreign Application Priority Data

Nov. 6, 1984 [JP] Japan .................................. 59-234697

[51] Int. Cl.$^4$ .................................. C07C 1/04
[52] U.S. Cl. .................................. 518/715; 502/304
[58] Field of Search .................................. 518/715

[56] References Cited

U.S. PATENT DOCUMENTS

| | | | |
|---|---|---|---|
| 3,322,491 | 5/1967 | Barrett et al. | 502/304 X |
| 3,888,792 | 6/1975 | Hughes | 502/304 X |
| 4,177,163 | 12/1979 | Oleck et al. | 502/304 X |
| 4,235,755 | 11/1980 | Antos | 502/304 X |
| 4,256,653 | 3/1981 | Atkinson | 518/715 |
| 4,487,851 | 12/1984 | Heyward et al. | 518/715 X |
| 4,613,624 | 9/1986 | Beuther et al. | 518/715 |

FOREIGN PATENT DOCUMENTS 895491  7/1981  U.S.S.R. .................. 518/715

OTHER PUBLICATIONS

Atkinson et al, U.S. Pat. Appl. 738,201, Nov. 3, 1976, CA 87 (1977) 141949z.
Kondo et al, Sekiyu Gakkaishi (1984) 27(6) 556-563, CA 102:27780r.
Fujitani et al, Jpn Kokai Tokkyo Koko 79 45693, Apr. 11, 1979, CA 91:28070a (1979).

Primary Examiner—Howard T. Mars
Attorney, Agent, or Firm—Oblon, Fisher, Spivak, McClelland & Maier

[57] ABSTRACT

A catalyst for synthesizing hydrocarbons such as butane etc. by hydrogenation of carbon monoxide, which comprises cobalt and cerium oxide as catalytic components supported on a conventional porous material, or cobalt as a catalytic component and cerium oxide as a support thereof. This catalyst can produce $C_1$ or more hydrocarbons and especially $C_5$ or more hydrocarbons in good yields.

7 Claims, No Drawings

CATALYST FOR HYDROCARBON SYNTHESIS

This application is a division of application Ser. No. 791,064, filed Oct. 24, 1985 now abandoned.

BACKGROUND OF THE INVENTION

1. Field of the Invention

This invention relates to catalysts for synthesizing hydrocarbons such as butane etc. by hydrogenation of carbon monoxide.

2. Description of the Prior Art

Heretofore, as the aforesaid catalysts for hydrocarbon synthesis employed on a commercial scale, there have been used the so-called Fischer-Tropsch synthetic catalysts, i.e., catalysts of nickel, cobalt, iron etc. supported on porous carriers or supports of e.g. silica, alumina, kieselguhr etc.

However, even such conventional catalysts can never be catalysts having satisfactory activity; for example, carbon deposits on a surface of the catalyst during the hydrocarbon synthetic process and the catalytic activity decreases.

In particular, $C_5^+$ (liquid hydrocarbons) which consist of 5 or more carbon atoms are useful as petroleum fuels, but catalysts having high activity for use in the synthesis of such liquid hydrocarbons have not yet been developed.

SUMMARY OF THE INVENTION

An object of this invention is to provide catalysts for hydrocarbon synthesis which have eliminated the above-described drawbacks inherent to the conventional techniques and have excellent activity.

Another object of this invention is to provide catalysts which can efficiently produce hydrocarbons, in particular liquid hydrocarbons of 5 or more carbon atoms.

Still another object of this invention is to provide catalysts not having carbon deposited on the surface during the hydrocarbon synthesis process and with high activity.

Accordingly, this invention resides in catalysts for synthesizing hydrocarbons by reducing carbon monoxide by hydrogen, which comprise cobalt and cerium oxide.

The above and other objects, features and advantages of the present invention will become more apparent from the following description in which a preferred embodiment of the invention is shown by way of illustrative example.

DETAILED DESCRIPTION

In this invention, the catalyst components, namely, cobalt and cerium oxide may be supported on a porous support or carrier such as kieselguhr, alumina ($Al_2O_3$), alumina-magnesia spinel ($MgAl_2O_4$), sepiolite etc. Alternatively, cerium oxide may be made into a porous support and cobalt supported on this porous support.

The form of the support is not particularly restricted and may be granules, plates, pellets, honeycombs etc. Further, it is preferred that the aforesaid support be a porous material and the average pore diameter of said porous material be in the range of 50 Å–2μ. Where the average pore diameter is out of the above range, it is difficult to provide excellent activity as a catalyst for hydrocarbon synthesis. The aforesaid porous support is prepared by, for example, molding its raw material powder into a desired shape and heating it to make a porous sintered material.

On supporting cobalt and cerium oxide, which are the catalyst components, on the aforesaid porous support, a method similar to the conventional method for supporting catalyst components may be conducted; for example, the aforesaid porous support is immersed in aqueous solutions of cobalt and cerium metal salts, such as cobalt nitrate, cerium nitrate, cobalt chloride, cerium chloride, cobalt sulfate, cerium sulfate etc., dried and calcined. By the aforesaid calcination, the metal salts become the corresponding catalyst components respectively. Of these catalyst components, cobalt is directly supported as a cobalt, while cerium is supported in the form of cerium oxide. Where both cobalt and cerium oxide are to be supported, for example, in a method of immersing a support in aqueous solutions of the aforesaid metal salts of cobalt and cerium, two different aqueous solutions may be used separately, or both may be simultaneously supported by using an aqueous solution containing a mixture of both metal salts. Also, where cerium oxide is used as a support, cobalt may be supported on a cerium oxide support in a manner similar to that described above.

On such supporting, where cobalt and cerium oxide are supported on a conventional porous support, the supporting amount is desirably such that cobalt be 3–15 % by weight and cerium oxide be 0.5–15 % by weight calculated as cerium, respectively relative to the porous support. If the supporting amount is less than the aforesaid ranges, sufficient catalyst activity cannot be obtained, whereas if beyond the aforesaid ranges, the catalyst activity as expected from the supported amounts cannot be obtained and even the cost is also increased. The ratio by weight of cobalt to cerium oxide (calculated as cerium) is desirably in the range of 0.5–10. However, if the aforesaid ratio by weight is out of the aforesaid range, the selectivity to $C_5$ or more hydrocarbons is low, and thus it is difficult to efficiently produce $C_5$ or more hydrocarbons. On the other hand, where cobalt is supported on a support of cerium oxide, the amount of cobalt supported is desirably in the range of 1–25% by weight relative to the cerium oxide support. With less than 1% by weight of said supported amount, sufficient activity cannot be obtained, whereas if the amount exceeds 25% by weight, the activity as expected from the supported amount cannot be obtained.

The catalysts according to this invention may be of any shape and structure, for example, granules, pellets, honeycombs etc. Said catalysts are desirably used at a reaction temperature of 100°–300° C. under a reaction pressure of 1–20 atms at a space velocity of 200–2000 $hr^{-1}$ as in the above-described conventional catalysts.

The catalysts according to this invention can efficiently reduce carbon monoxide by hydrogen and produce $C_1$ or more hydrocarbons such as methane, butane etc. in good yields, especially can produce $C_5$ or more liquid hydrocarbons in good yields.

Further, with the catalysts according to this invention, cerium oxide per se which is one of the catalyst components may be used as a support, not to mention the conventional porous supports.

Still further, the catalysts of this invention may be prepared by merely impregnating the aforesaid supports with the catalyst components and hence the process for the preparation of catalysts is easy and also the reproducibility of the catalytic activity (conversion, selectivity) is excellent. In addition, the hydrocarbon synthetic reaction using the catalysts of this invention is carried out without the deposition of carbon on the catalysts and thus the decrease in the catalyst activity is low.

This invention is more particularly described by the following examples.

EXAMPLE 1

Using cerium oxide per se as a support, catalysts of cobalt supported on such a support were prepared.

More specifically, the aforesaid cerium oxide ($CeO_2$) support was prepared by calcining cerium nitrate in the air at 600° C. for 3 hours to convert it to cerium oxide and molding into pellets of 3 mm in diameter (the pore volume, average pore diameter and surface area of this support are shown in Table 1, Support No. 1).

Thereafter, the aforesaid $CeO_2$ support was immersed in aqueous cobalt nitrate solutions at the various predetermined concentrations for 30 minutes respectively. Then, after sufficiently removing the mother liquors, the residues were dried at 110° C. for 10 hours and subsequently calcined at 400° C. for 3 hours. Thereby, cobalt (Co) supporting catalysts according to this invention in the form of pellets of 3 mm in diameter were prepared (Catalyst No. 1-7 in Table 2).

For comparison, using γ-alumina ($Al_2O_3$), α-alumina ($Al_2O_3$) and silica ($SiO_2$) as supports respectively, comparative catalysts in the form of pellets of 2-3 mm in diameter were prepared in a similar manner to the above mentioned by supporting cobalt on these supports respectively (Catalyst No. $A_1$-$A_3$ in Table 2). The pore volume, average pore diameter and surface area of each support are shown in Support No. $S_1$-$S_3$ in Table 1.

Thereafter, the catalytic activity of the above catalysts was evaluated. The evaluation of the catalytic activity was conducted by filling 20 ml of the catalyst in a stainless steel reaction tube of 18 mm in inner diameter, reducing by hydrogen at 350° C. for an hour, then, introducing a mixed gas of a molar ratio of hydrogen ($H_2$) to carbon monoxide (CO) of 3 into this reaction tube at a reaction temperature of 220° C. under a reaction pressure of 5 kg/cm$^2$ (gauge) for a contact time of 68.1 hr·g/CO mole, and measuring the conversion of carbon monoxide and the amount of hydrocarbons in the reaction product. The conversion of carbon monoxide as used herein means the proportion (%) of carbon monoxide converted to other substances. Further, the hydrocarbons produced by such conversion and present in the reaction product were measured by gas chromatogram for $C_5$ or more hydrocarbons as indicated by the amount of carbon per molecule of hydrocarbon, together with the amounts of CO and $CO_2$. The aforesaid $C_5$ means pentane etc.

The results of these measurements are shown in Table 2. As can be seen from Table 2, the conversion of CO by the catalysts of this invention and the amounts of $C_5$ or more hydrocarbons produced thereby are greater than the values by the comparative catalysts, and thus the catalysts according to this invention have superior catalytic activity as compared with the comparative catalysts.

TABLE 1

| Support No. | Material | Pore Volume (cm$^3$g) | Average Pore Diameter (Å) | Surface Area (m$^2$/g) |
|---|---|---|---|---|
| 1 | $CeO_2$ | 0.8 | 200 | 60 |
| $S_1$ | γ-$Al_2O_3$ | 0.51 | 120 | 165 |
| $S_2$ | α-$Al_2O_3$ | 0.52 | 1000 | 11 |
| $S_3$ | $SiO_2$ | 1.2 | 50 | 300 |

TABLE 2

| Catalyst No. | 1 | 2 | 3 | 4 | 5 | 6 | 7 | $A_1$ | $A_2$ | $A_3$ |
|---|---|---|---|---|---|---|---|---|---|---|
| Support No. | 1 | 1 | 1 | 1 | 1 | 1 | 1 | $S_1$ | $S_2$ | $S_3$ |
| Amount of Co Supported (% by weight) | 2 | 4 | 6 | 8 | 10 | 15 | 20 | 4 | 4 | 4 |
| Conversion of Co (%) | 72 | 75 | 81 | 80 | 74 | 70 | 71 | 21 | 5 | 30 |
| Amounts of $C_5$ or more Hydrocarbons Produced (g/hr · kg · cat) | 37 | 35 | 32 | 33 | 40 | 36 | 34 | 17 | 4 | 23 |
| | Present Invention | | | | | | | Comparative Examples | | |

EXAMPLE 2

Using alumina.magnesia spinel ($MgAl_2O_3$) as a support, catalysts were prepared by supporting cobalt and cerium oxide on such a support.

More specifically, this spinel support was prepared by mixing 55 mole % of alumina and 45 mole % of magnesia and sintering at 1350° C. This support was in the form of pellets of 2-3 mm in diameter and having a pore volume of 0.41 cm$^3$/g, an average pore diameter of 2900 Å and a surface area of 15 m$^2$/g, and its structure as of a spinel structure.

Thereafter, using mixed aqueous solutions of cerium nitrate and cobalt nitrate at the various predetermined concentrations respectively, cerium oxide and cobalt were supported on the above spinel support in a manner similar to that in Example 1 to prepare catalysts according to this invention (Catalyst No. 8-14 in Table 3) (the amount of cerium oxide supported in Table 3 is that calculated as cerium (Ce)).

For comparison, a catalyst comprising cobalt alone supported on the same spinel support (Catalyst No. $A_4$ in Table 3) was also prepared.

The thus obtained catalysts were measured for the catalytic activity under similar conditions to those in Example 1, except that the reaction pressure was changed to 10 kg/cm$^2$ (gauge). The results of the measurements are shown in Table 3.

As can be seen from Table 3, the catalysts according to this invention have superior conversion of Co and produce greater amounts of $C_5$ or more hydrocarbons as compared with the comparative catalysts, and thus are excellent catalysts.

TABLE 3

| Catalyst No. | 8 | 9 | 10 | 11 | 12 | 13 | 14 | $A_4$ |
|---|---|---|---|---|---|---|---|---|
| Amount Supported (% by weight) | | | | | | | | |
| Ce | 0.8 | 3.2 | 6.4 | 12.8 | 12.8 | 12.8 | 12.8 | — |
| Co | 4 | 4 | 4 | 4 | 6 | 8 | 12 | 4 |
| Conversion of CO (%) | 39 | 44 | 45 | 44 | 45 | 47 | 46 | 31 |
| Amounts of $C_5$ or more Hydrocarbons Produced | 68 | 75 | 73 | 81 | 76 | 78 | 78 | 56 |

TABLE 3-continued (g/hr · kg · cat)

| | Present Invention | Comparative Example |
|---|---|---|

What is claimed is:

1. A method of synthesizing liquid hydrocarbons having at least 5 carbon atoms, which comprises:
   preparing a catalyst consisting essentially of cobalt and cerium oxide as catalyst components, said cerium oxide being porous, and said cobalt being supported on said porous cerium oxide in an amount ranging from 1 to 25% by weight relative to said cerium oxide; and
   reacting a mixture of hydrogen and carbon monoxide over said catalyst so as to synthesize liquid hydrocarbons having at least 5 carbon atoms, said reaction being conducted at a temperature ranging from 100° C.-300° C. under a pressure of 1-20 atmospheres at a space velocity of 200-2000 hr$^{-1}$.

2. The method according to claim 1, wherein the amount of said cobalt ranges from 4 to 10% by weight relative to said cerium oxide.

3. The method according to claim 1, wherein said porous cerium oxide support has an average pore size diameter ranging from 50 Å to 2 μm.

4. A method of synthesizing liquid hydrocarbons having at least 5 carbon atoms, which comprises:
   preparing a catalyst consisting essentially of cobalt and cerium oxide as catalyst components; and
   reacting a mixture of hydrogen and carbon monoxide over said catalyst so as to synthesize liquid hydrocarbons having at least 5 carbon atoms, said cobalt and cerium oxide being supported on a porous support of alumina.magnesia spinel, and the amount of said cobalt ranging from 3 to 15% by weight and that of said cerium oxide ranging from 0.5 to 15% by weight calculated as cerium, each relative to said porous support, the weight ratio of said cobalt to said cerium oxide calculated as cerium ranging from 0.5 to 10.

5. The method according to claim 39, wherein the amount of said cobalt ranges from 4 to 8% by weight and that of said cerium oxide ranges from 6.4 to 12.8% by weight calculated as cerium, each relative to said porous support.

6. The method according to claim 39, wherein said porous support has an average pore size diameter ranging from 50 Å to 2 μm.

7. The method according to claim 39, wherein the amounts of said cobalt and said cerium oxide are 4% by weight and 12.8% by weight calculated as cerium, respectively, relative to said porous support.

* * * * *

UNITED STATES PATENT AND TRADEMARK OFFICE
CERTIFICATE OF CORRECTION

PATENT NO. : 4,801,620
DATED : January 31, 1989
INVENTOR(S) : YOSHIYASU FUJITANI ET AL It is certified that error appears in the above-identified patent and that said Letters Patent is hereby corrected as shown below:

| COL | LINE | |
|---|---|---|
| 6 | 20 | Delete "39" and insert --4--, |
| 6 | 25 | Delete "39" and insert --4--, |
| 6 | 28 | Delete "39" and insert --4--. |

Signed and Sealed this

Tenth Day of July, 1990

Attest:

HARRY F. MANBECK, JR.

*Attesting Officer*   *Commissioner of Patents and Trademarks*